(12) United States Patent
Sirohey et al.

(10) Patent No.: US 7,929,737 B2
(45) Date of Patent: Apr. 19, 2011

(54) METHOD AND SYSTEM FOR AUTOMATICALLY GENERATING A DISEASE SEVERITY INDEX

(75) Inventors: Saad Ahmed Sirohey, Pewaukee, WI (US); Gopal B. Avinash, New Berlin, WI (US); Tamanna Bembenek, Milwaukee, WI (US)

(73) Assignee: General Electric Company, Niskayuna, NY (US)

( * ) Notice: Subject to any disclaimer, the term of this patent is extended or adjusted under 35 U.S.C. 154(b) by 1031 days.

(21) Appl. No.: 11/523,878

(22) Filed: Sep. 20, 2006

(65) Prior Publication Data

US 2007/0081707 A1 Apr. 12, 2007

Related U.S. Application Data

(63) Continuation-in-part of application No. 11/241,570, filed on Sep. 29, 2005, which is a continuation-in-part of application No. 11/240,610, filed on Sep. 29, 2005, which is a continuation-in-part of application No. 11/240,609, filed on Sep. 29, 2005.

(51) Int. Cl.
G06K 9/00 (2006.01)

(52) U.S. Cl. ............................................. 382/128

(58) Field of Classification Search ............... 382/132, 382/128, 282, 209, 195; 600/407, 300
See application file for complete search history.

(56) References Cited

U.S. PATENT DOCUMENTS

| | | | |
|---|---|---|---|
| 4,170,987 A | 10/1979 | Anselmo et al. | |
| 4,839,807 A | 6/1989 | Doi et al. | |
| 5,109,868 A | 5/1992 | Smith et al. | |
| 5,262,945 A | 11/1993 | DeCarli et al. | |
| 5,434,050 A | 7/1995 | Maggio et al. | |
| 5,617,861 A | 4/1997 | Ross et al. | |
| 5,632,276 A | 5/1997 | Eidelberg et al. | |
| 5,873,823 A | 2/1999 | Eidelberg et al. | |
| 6,173,068 B1 | 1/2001 | Prokoski | |
| 6,306,087 B1 * | 10/2001 | Barnhill et al. | 600/300 |
| 6,374,130 B1 | 4/2002 | Reiman | |
| 6,430,430 B1 | 8/2002 | Gosche | |
| 6,484,047 B1 | 11/2002 | Vilsmeier | |
| 6,490,472 B1 | 12/2002 | Li et al. | |
| 6,581,011 B1 | 6/2003 | Johnson et al. | |
| 6,622,036 B1 | 9/2003 | Suffin | |
| 6,690,816 B2 | 2/2004 | Aylward et al. | |

(Continued)

FOREIGN PATENT DOCUMENTS

JP 9147082 6/1997

*Primary Examiner* — Anand Bhatnagar
*Assistant Examiner* — Claire Wang
(74) *Attorney, Agent, or Firm* — Fletcher Yoder

(57) ABSTRACT

Methods and systems for automatically generating a severity index for images of anatomical features of a patient are provided. In an exemplary embodiment, an image of an anatomical feature of a patient is compared with a normal, standardized image of the same anatomical feature. Based on this comparison, a deviation image for the anatomical feature is generated that represents the degree and manner the acquired image deviates from normal for that anatomical feature. The deviation image is automatically pattern matched against multiple images of known disease severity for the anatomical feature. Based on the automated pattern match, a known disease severity, such as in the form of a severity index, is provided as corresponding anatomical feature for the patient.

21 Claims, 10 Drawing Sheets

U.S. PATENT DOCUMENTS

| | | |
|---|---|---|
| 6,907,280 B2 | 6/2005 | Becerra et al. |
| 6,996,261 B2 | 2/2006 | deCharms |
| 7,184,582 B2 | 2/2007 | Giger et al. |
| 2002/0058867 A1 | 5/2002 | Breiter et al. |
| 2002/0086347 A1 | 7/2002 | Johnson et al. |
| 2003/0053673 A1* | 3/2003 | Dewaele .................. 382/132 |
| 2003/0095692 A1 | 5/2003 | Mundy et al. |
| 2004/0092809 A1 | 5/2004 | deCharms |
| 2005/0065421 A1* | 3/2005 | Burckhardt ............... 600/407 |
| 2005/0085705 A1 | 4/2005 | Rao et al. |
| 2005/0215889 A1 | 9/2005 | Patterson, II |
| 2006/0074290 A1 | 4/2006 | Chen et al. |
| 2006/0088614 A1 | 4/2006 | Pettegrew et al. |
| 2006/0292547 A1 | 12/2006 | Pettegrew et al. |
| 2007/0003117 A1 | 1/2007 | Wheeler et al. |
| 2007/0019846 A1 | 1/2007 | Bullitt et al. |
| 2007/0081699 A1 | 4/2007 | Avinash et al. |
| 2007/0081700 A1 | 4/2007 | Blumenfeld et al. |
| 2007/0081701 A1* | 4/2007 | Sirohey et al. ............ 382/128 |
| 2007/0218002 A1 | 9/2007 | Barrio et al. |

* cited by examiner

METHOD AND SYSTEM FOR AUTOMATICALLY GENERATING A DISEASE SEVERITY INDEX

CROSS REFERENCE TO RELATED APPLICATIONS

This application is a continuation-in-part of U.S. patent application Ser. No. 11/241,570, filed Sep. 29, 2005, and entitled "SYSTEMS, METHODS AND APPARATUS FOR TRACKING PROGRESSION AND TRACKING TREATMENT OF DISEASE FROM CATEGORICAL INDICES" and of U.S. patent application Ser. No. 11/240,610, filed Sep. 29, 2005, and entitled "SYSTEMS, METHODS AND APPARATUS FOR CREATION OF A DATABASE OF IMAGES FROM CATEGORICAL INDICES", and of U.S. patent application Ser. No. 11/240,609, filed Sep. 29, 2005, and entitled "SYSTEMS, METHODS AND APPARATUS FOR DIAGNOSIS OF DISEASE FROM CATEGORICAL INDICES", all of which are incorporated by reference in their entirety.

BACKGROUND

This invention relates generally to medical diagnosis, and more particularly to the automated diagnosis of medical conditions from images of a patient.

One type of medical condition or disease that is of interest to the medical community are neurodegenerative disorders (NDDs). However, NDDs may be challenging to treat and/or study because they are both difficult to detect at an early stage and hard to quantify in a standardized manner for comparison across different patient populations. In response to these difficulties, investigators have developed methods to determine statistical deviations from normal patient populations.

These earlier methods include transforming patient images using two types of standardizations, anatomical and intensity. Anatomical standardization transforms the images from the patient's coordinate system to a standardized reference coordinate system. Intensity standardization involves adjusting the patient's images to have equivalent intensity to reference images. The resulting transformed images may then be compared to a reference database. The database includes age and tracer specific reference data. Most of the resulting analysis takes the form of point-wise or region-wise statistical deviations, typically depicted as Z scores. In some embodiments, the tracer is a radioactive tracer used in nuclear imaging.

One element of the detection of NDD is the development of age and tracer segregated normal databases. Comparison to these normals can only happen in a standardized domain, e.g. the Talairach domain or the Montreal Neurological Institute (MNI) domain. The MNI defines a standard brain by using a large series of magnetic resonance imaging (MRI) scans on normal controls. The Talairach domain is references a brain that is dissected and photographed for the Talairach and Tournoux atlas. In both the Talairach domain and the MNI domain, data must be mapped to the respective standard domain using registration techniques. Current methods that use a variation of the above method include tracers NeuroQ®, Statistical Parametric matching (SPM), 3D-sterotactic surface projections (3D-SSP), and so forth.

Once a comparison has been made, an image representing a statistical deviation of the anatomy is displayed, allowing a viewer to make a diagnosis based on the image. Making such a diagnosis is a very specialized task and is typically performed by highly trained medical image experts. However, even such experts can only make a subjective call as to the degree of severity of the disease. Due to this inherent subjectivity, the diagnoses tend to be inconsistent and non-standardized. It may, therefore, be desirable to increase the consistency and standardization of such diagnoses.

BRIEF DESCRIPTION

The present invention provides novel techniques for automatically generating a severity index for images of anatomical features of a patient, typically acquired using tracers. For example, an image of an anatomical feature of a patient may be compared with a normal, standardized image of the same anatomical feature. Based on this comparison, a deviation image for the anatomical feature may be generated that represents the degree and manner the acquired image deviates from normal for that anatomical feature. The deviation image is automatically pattern matched against multiple images of known disease severity for the anatomical feature. Based on the automated pattern match, a known disease severity, such as in the form of a severity index, may be provided as corresponding anatomical feature for the patient.

The invention may be performed in serial or parallel for multiple anatomical features of the patient, thereby generating multiple severity indices for the different, respective anatomical features. In such a case, an overall or aggregate severity score may be generated, such as using a rules-based technique, that sums or otherwise combines the various severity indices into a single score for the patient.

In one embodiment, therefore, the present technique provides a method to create a normative categorical score of medical diagnostic images. The method includes the act of accessing image data of at least one specific anatomical region. The anatomical image data is consistent with an indication of functional information in reference to at least one tracer in the anatomical region at the time of the imaging. Deviation severity data is determined from the anatomical image data and from normative standardized anatomical image data based on one or more subject specific factors. The deviation severity data for each of the at least one anatomical region is automatically matched with an image severity deviation that is categorized into a degree of severity for each of the at least one anatomical region. A severity index is automatically assigned to each of the deviation severity data for each of the at least one anatomical region. Each severity index is assigned based on the image severity deviation for the respective anatomical region that is automatically matched with each respective deviation severity data. Corresponding claims to one or more tangible, machine readable media, comprising code executable to perform these acts are also provided.

In another embodiment, the present technique provides a method for automatically generating a severity score. The method includes the act of automatically generating a severity index for each of a plurality of patient images. A severity score is automatically derived based on the plurality of severity indexes.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

System Level Overview

Figure 1:
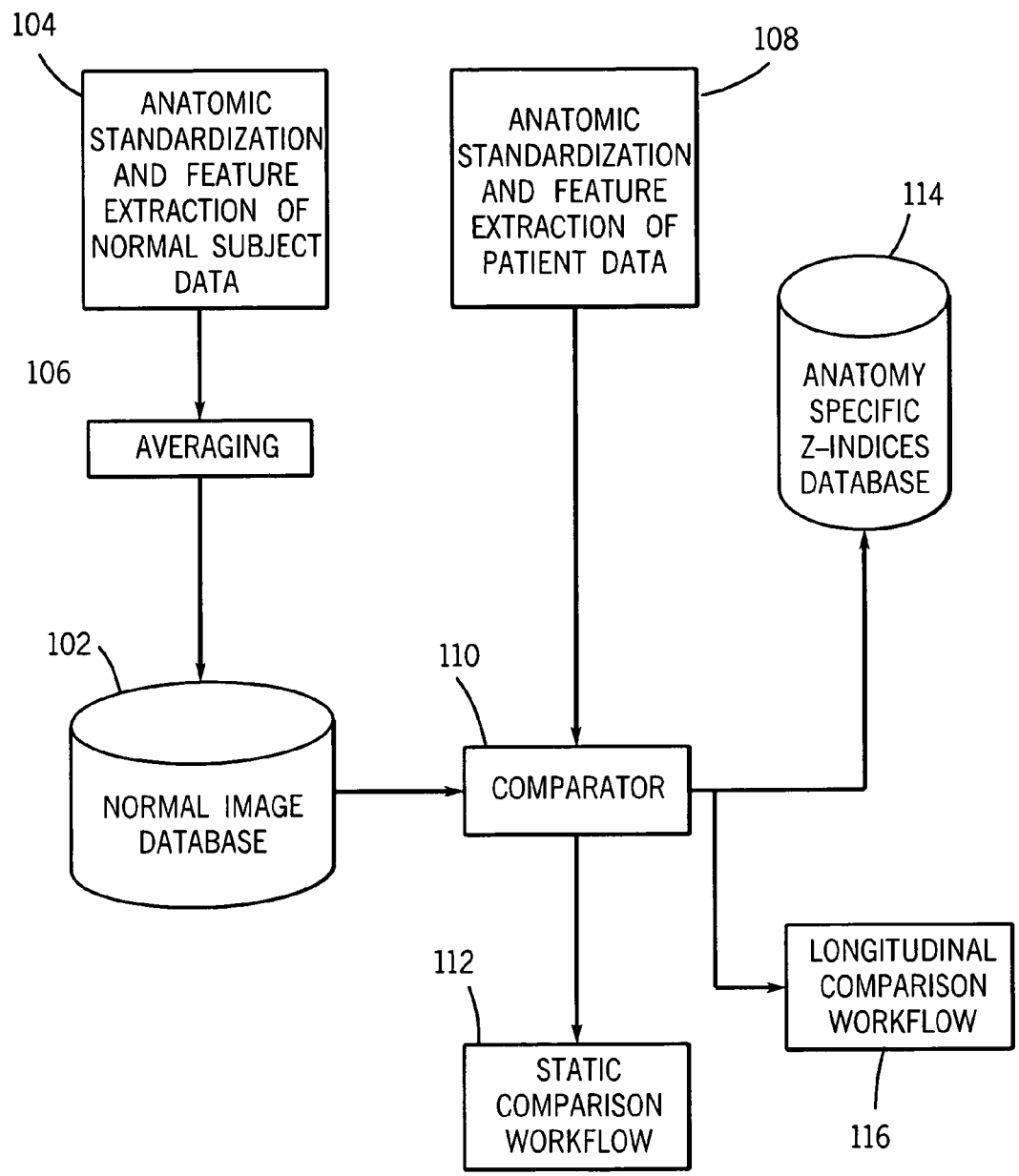
FIG. 1 is a block diagram of an overview of a system to determine statistical deviations from normal patient populations, in accordance with aspects of the present technique.

FIG. 1 is a generalized block diagram of a system to determine statistical deviations from normal patient populations. System 100 includes a normal image database 102 that includes images of non-diseased anatomical structures. The normal image database 102 provides a baseline for comparison to help identify images of diseased anatomical structures, thereby providing more consistent, formalized and reliable diagnoses of medical conditions and diseases from medical anatomical images.

In some embodiments, the normal image database 102 is generated by a component 104 that standardizes normal anatomic images and extracts anatomic features. In the depicted exemplary embodiment, a component 106 averages the extracted anatomic feature images as part of forming the normal image database 102. As will be appreciated by those of ordinary skill in the art, other combinatorial or statistical techniques may also be employed by the component 106 in forming the normal image database 102 from the extracted features. The averaged anatomic feature images constituting the normal image database 102 are sufficiently within the range of typical non-diseased anatomic features to be considered as normal anatomic features.

In one embodiment, patient specific data is generated by the system 100 by a component 108 that standardizes anatomic images of a patient and extracts anatomic features of the standardized patient image. In an exemplary embodiment, the image(s) of extracted anatomic features and the images in the normal image database 102 are encoded in a format that allows for comparison.

The image(s) of the extracted anatomic features and the images in the normal image database 102 are compared by a component 110 of the system 100. In some embodiments, a pixel-by-pixel comparison is performed by the component 110. In one embodiment, the comparison yields a static comparison workflow 112, described in greater detail in FIG. 3. In some embodiments, the comparison yields or updates a database 114 of Z-scores that are specific to a particular anatomic feature. In some embodiments, the comparison yields a longitudinal, i.e., temporal, comparison workflow 116. A longitudinal comparison compares images over a time interval. The system 100 is depicted as being capable of generating a static comparison workflow 112, a database 114 of Z-scores, and a longitudinal comparison workflow 116. However, as will be appreciated by those of ordinary skill in the art, the system 100 need not generate all three types of analysis for each patient. Instead, operator preference, clinical custom, patient specific factors, or other considerations may determine if one, two, or all of these types of results are generated for a particular patient during a particular examination.

Figure 12:
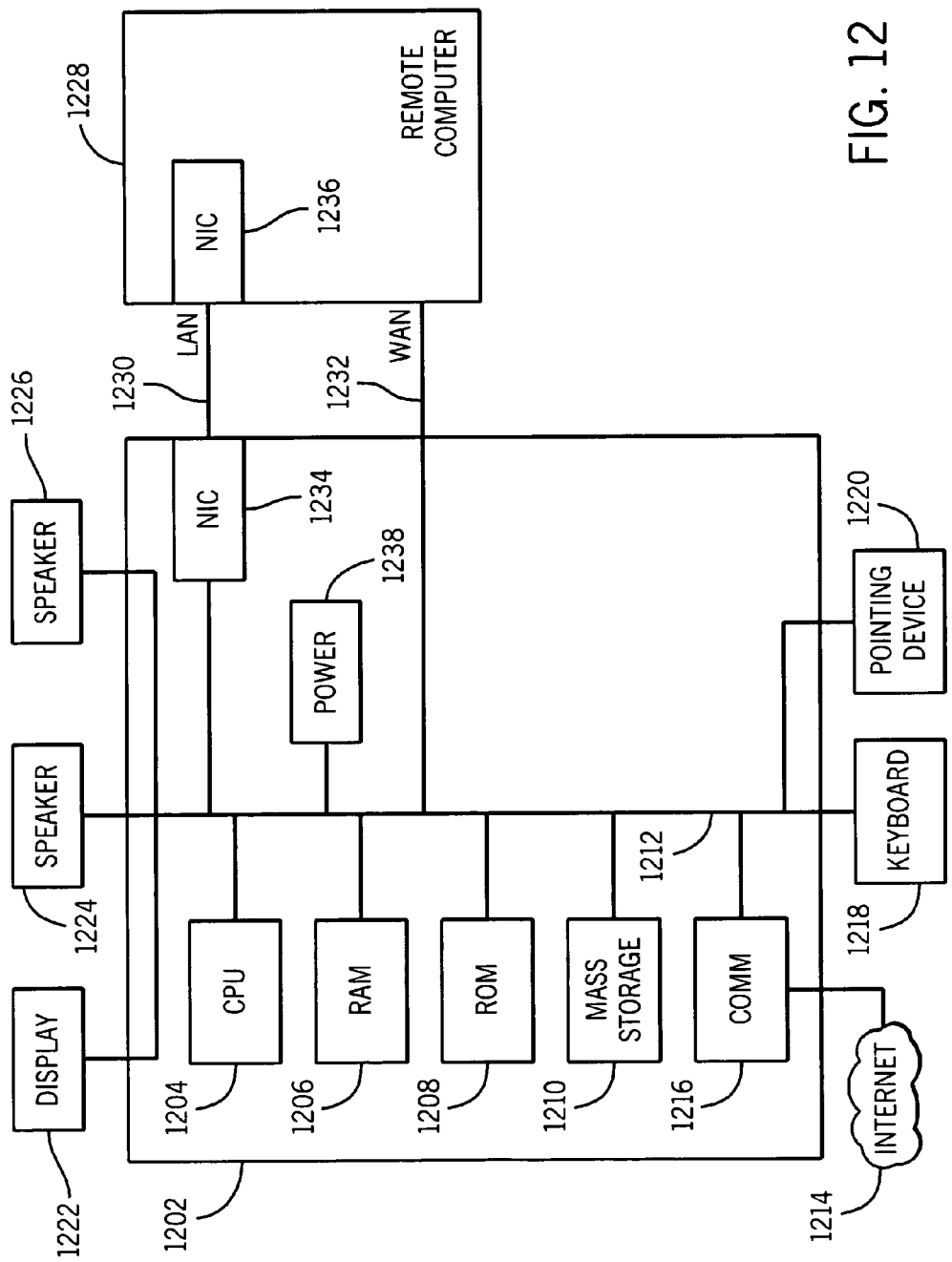
FIG. 12 is a block diagram of the hardware and operating environment in which different embodiments of the present technique can be practiced.

Some embodiments operate in a multi-processing, multi-threaded operating environment on a computer, such as computer 1202 in FIG. 12. However, the system 100 is not limited to any particular normal image database 102, or with regard to the hardware, firmware, software or circuitry that performs, stores or displays the standardization, extraction, and/or comparison functions or the workflow and/or Z-indices results. Instead, as will be appreciated by those of ordinary skill in the art, processors, memory components, displays and so forth typically suitable for image and data processing are suitable for use in the system 100 of FIG. 1 as the described components 104, 106, 108, 110.

Method Embodiments

In the previous section, a system level overview of the operation of an exemplary embodiment is described. In this section, the particular user-performed and automated steps of such an exemplary embodiment are described by reference to the accompanying flowcharts. Describing the methods by reference to a flowchart enables one skilled in the art to develop programs, firmware, and/or hardware using computer-readable instructions executable on suitable processor-based systems. For example, the following techniques described by flowcharts may be encoded as computer-readable routines that may be executed on a processor-based system such as the computer 1202 of FIG. 12.

Figure 2:
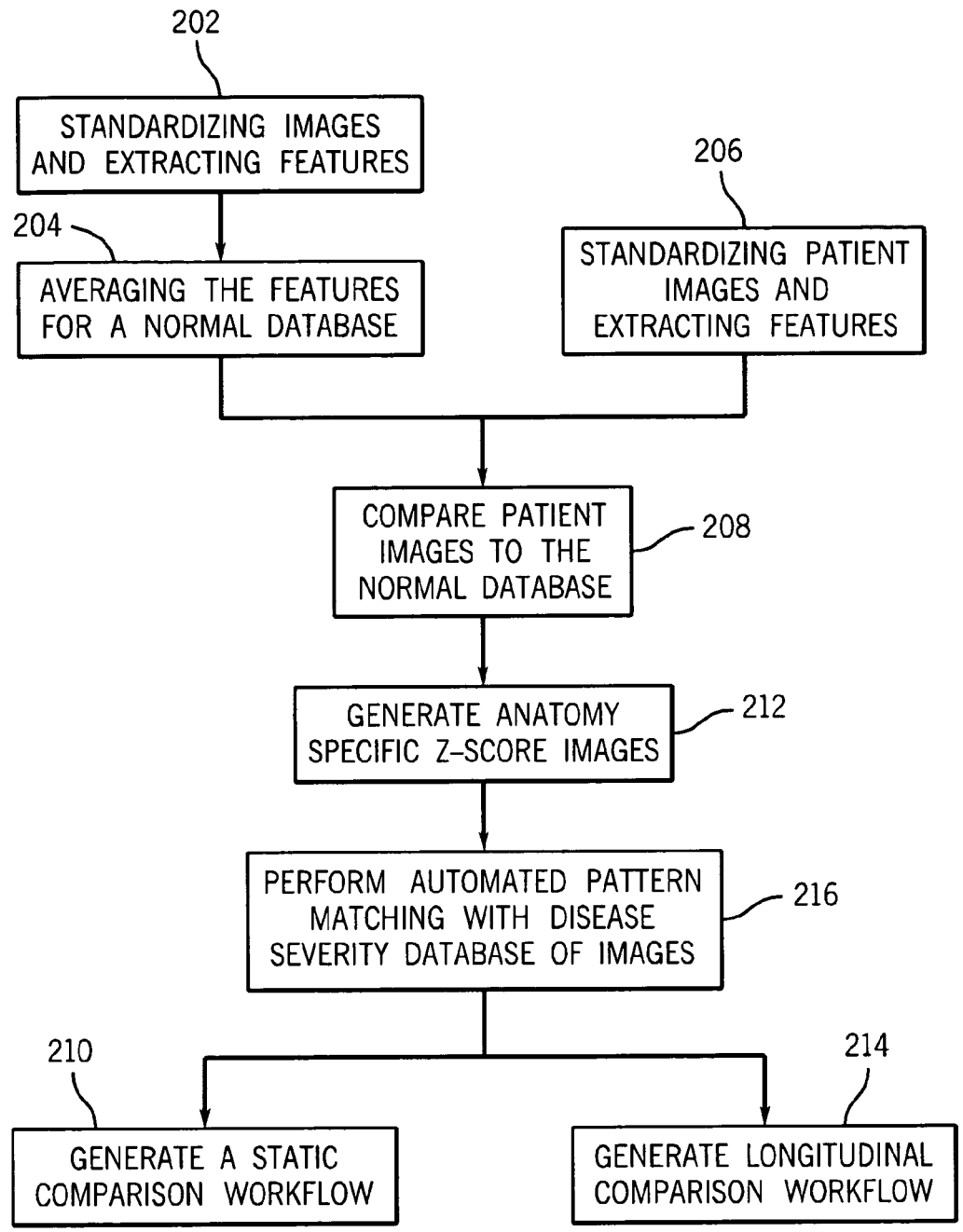
FIG. 2 is a flowchart of a method to determine statistical deviations from normal patient populations, in accordance with aspects of the present technique.

Turning now to FIG. 2, a flowchart is provided describing a method 200 for determining statistical deviations from normal patient populations, as briefly noted with regard to the system of FIG. 1. The method 200 includes standardizing normal anatomic images and extracting anatomic features (Block 202). In some embodiments, the act of standardizing includes mapping the normal anatomic images to a defined atlas/coordinate system such as to the Talairach or Montreal Neurological Institute (MNI) domains. In the depicted embodiment, method 200 also includes averaging (Block 204) the extracted anatomic feature images to populate a database of normal, non-diseased anatomic features (such as database 102 of FIG. 1).

In the depicted embodiment, anatomic images of a patient are also standardized and anatomic features extracted from the standardized patient images (Block 206). The image(s) of the extracted patient anatomic features and the normative standardized anatomical images in the normal image database are compared (Block 208), such as on a pixel-by-pixel basis, as noted above.

As a result of the comparison 208, anatomy specific deviation data, i.e., Z-score images, are generated (Block 212). As will be appreciated by those of ordinary skill in the art, such deviation data may be used to generate or update an anatomy specific Z-indices database of FIG. 1. In an exemplary embodiment, the deviation data are automatically matched (Block 216) using pattern matching with corresponding images of the anatomical feature representing different, known disease states for the anatomical features, i.e., disease severity deviation images. In this manner, each deviation data may be automatically matched to a corresponding disease severity deviation images for the respective anatomical feature. In one embodiment, this disease state or severity may take the form of a severity index for the anatomical feature.

The results of the automated matching process may then be used to generate a static comparison workflow (Block 210) or to generate a longitudinal comparison workflow (Block 214) which may in turn be present to a user to review or evaluate. As noted above, depending on the patient and/or on the clinical circumstances or practice, only some or all of these results may be generated in a particular case.

Figure 3:
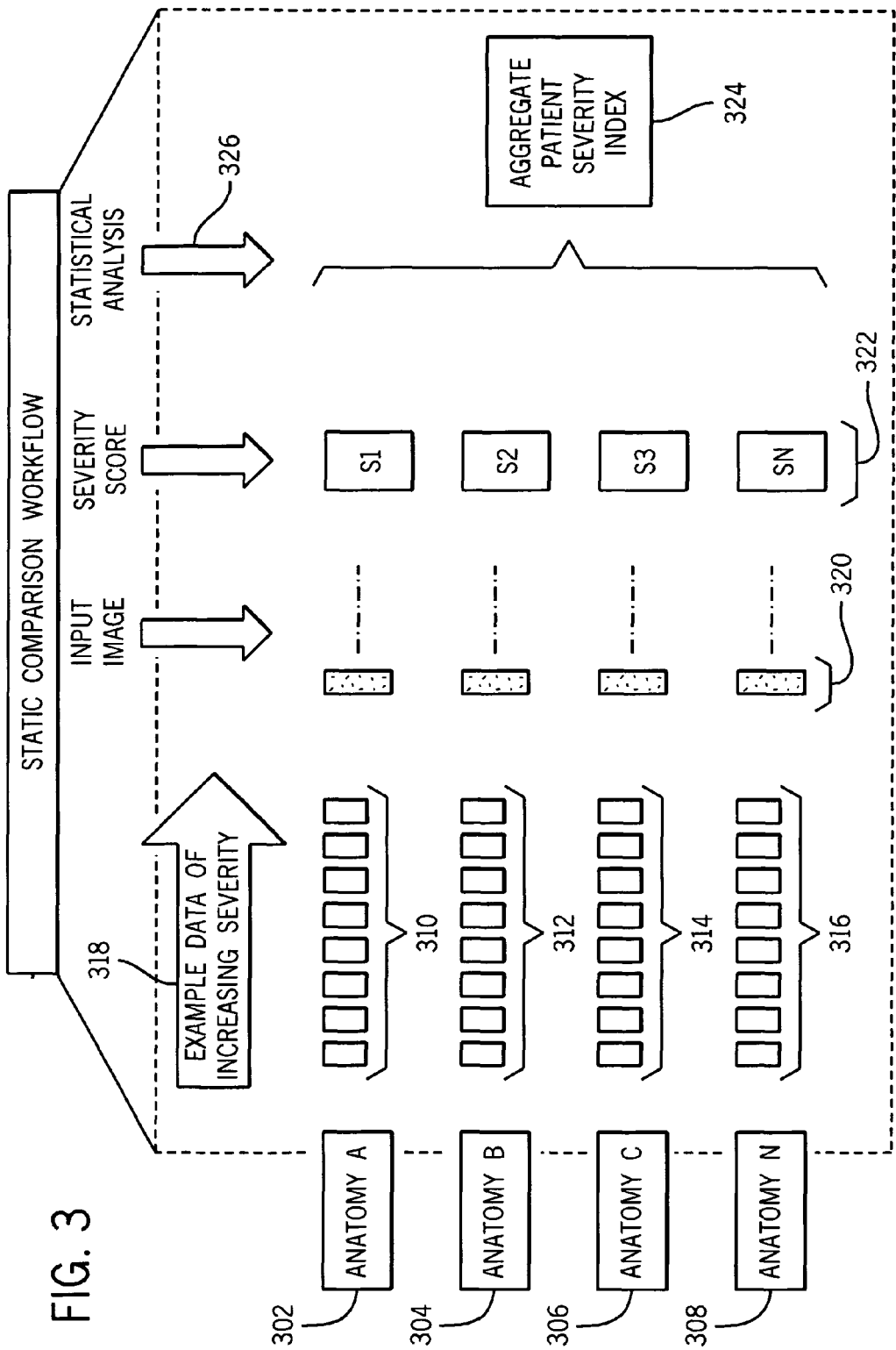
FIG. 3 is a diagram of a static comparison workflow to automatically determine a severity index, in accordance with aspects of the present technique.

FIG. 3 is an exemplary diagram of a static comparison workflow 112 (FIG. 1) exemplifying the automatic generation of a severity index for each anatomical feature of interest. The static comparison workflow 112 may encompass a number of anatomical features, such as features of a brain and/or heart. To depict the possibility of such a multitude of anatomical features in a comparison, the static comparison workflow 112 is depicted as including a first anatomical feature "A" 302, a second anatomical feature "B" 304, a third anatomical feature "C" 306, an "N'th" anatomical feature "N" 308, and so forth. The static workflow comparison of FIG. 3 represents a specific implementation of the more generalized matching and presentation techniques described in U.S. patent application Ser. No. 11/240,880 titled "COMPUTER ASSISTED DOMAIN SPECIFIC ENTITY MAPPING METHOD AND SYSTEM" and filed on Sep. 30, 2005, hereby incorporated by reference in its entirety. For example, in this specific implementation the various anatomical features 302, 304, 306, 308 represent various axes while the disease severity deviation images 310, 312, 314, 316 discussed below represent different labels associated with each axis, and so forth.

For each anatomical feature, a number of images having variations in the extent of a disease or a condition are provided. For example, for anatomical feature "A" 302, a number of images 310 having variations in the extent of a disease or a condition associated with anatomical feature "A" are provided. Similarly, images 312, 314, and 316 are provided which exhibit the variations in the extent of a disease or condition for each of the remaining respective anatomical features through the Nth feature. As will be appreciated by those of ordinary skill in the art, each of the disease severity deviation images within the respective image sets 310, 312, 314, 316 are generated for the respective anatomical feature 302, 304, 306, 308 and may be further categorized by a tracer or tracers (if one was employed) and by imaging technology employed. For example, images within the respective image sets 310, 312, 314, 316 may be generated by magnetic resonance imaging (MRI), positron emission tomography (PET), computed tomography (CT), single photon emission-computed tomography (SPECT), ultrasound, optical imaging, or other conventional imaging techniques and by using suitable tracers in appropriate circumstances.

For each anatomical feature, the disease severity deviation images 310, 312, 314, 316 of the anatomical features are ordered 318 according to the severity of the disease or condition or otherwise associated with a severity of the disease or condition. For example, for anatomical feature "A" 302, the disease severity deviation images 310 may be ordered in ascending order from the least extent or amount of the disease or condition, to the highest amount or extent of the disease or condition.

In the depicted embodiment, eight images are depicted in each of disease severity deviation image groups 310, 312, 314, 316 as representing the various disease severity levels associated with each anatomical feature 302, 304, 306, 308. As will be appreciated by those of ordinary skill in the art, however, the number of images in the sets of disease severity deviation images 310, 312, 314, 316 is arbitrary and can be increased or decreased depending on the implementation and the characteristics of the reviewer. For example, in exemplary embodiments where the comparison process is automated, the number of images within each of the groups of disease severity deviation images 310, 312, 314, 316 may contain more than eight images, such as ten, twenty, one hundred, and so forth. Further, though a single disease severity deviation image is presently depicted as corresponding to each ordered severity level for each anatomical feature, each degree of severity for each anatomical feature may actually have one or more than one disease severity deviation image provided for comparison. For example, in exemplary implementations where the comparison process is automated, each severity level or severity index for an anatomical feature 302, 304, 306, 308 may be represented by more than one disease severity deviation image.

One or more images of deviation data 320 may then be evaluated relative to the respective disease severity deviation images 310, 312, 314, 316 to determine an extent of disease or condition in the deviation data 320 in comparison to the respective disease severity deviation images. As mentioned above, each image of deviation data 320 for an anatomical feature may be generated by comparing an acquired image to a normative standardized anatomical image for the respective anatomical feature. As will be appreciated by those of ordinary skill in the art, the deviation data 320 may be derived from images acquired using one or more suitable tracers, when needed to capture desired functional information, and by using a conventional imaging technique, as described above. Therefore, in an exemplary embodiment, the deviation data 320 is not only compared to a set of disease severity deviation images 310, 312, 314, 316 corresponding to the same anatomical feature 302, 304, 306, 308, but also to those images in the set of disease severity deviation images 310, 312, 314, 316 acquired using the same or a comparable tracer or tracers, if present, and using the same or a comparable imaging technology. In an exemplary embodiment, the comparison between the one or more images of deviation data 320 and the respective set of disease severity deviation images 310, 312, 314, 316 is performed automatically, such as by pattern matching or other suitable comparison techniques and routines. In such an embodiment, the automatic matching process typically involves segmentation of the deviation data to identify one or more region of interest (such as masses or lesions), extracting features for comparison from the regions of interest, matching the extracted features with features in one or more corresponding disease severity images for the anatomical feature, and classifying the extracted features based upon the match.

For example, in one implementation deviation data 320 corresponding to the anatomical feature "A" 302 may be automatically compared to the corresponding set of ordered disease severity deviation images 310 that were acquired using the same tracer or tracers, if a tracer was employed, and using the same imaging modality, such as MRI or PET. As will be appreciated by those of ordinary skill in the art, deviation data 320 and the respective disease severity deviation images 310, 312, 314, 316 to which they are compared may vary depending on patient specific factors (such as patient history, patient symptoms, and so forth) as well as clinical factors (such as standard practice for the attending physician and for the medical facility, preliminary diagnoses, years of practice, and so forth).

In the depicted example, each comparison generates a severity index 322 that expresses or represents the extent of disease in the respective deviation data 320, as determine by comparison to the anatomical feature specific disease severity deviation images 310, 312, 314, 316. As will be appreciated by those of skill in the art, in those embodiments, in which the comparison is performed automatically, the severity index 322 is also, therefore, generated automatically. In such embodiments, a reviewer or evaluator may simply be provided with a severity index 322 for each anatomical feature of interest or for which deviation data 320 was acquired or submitted.

In some embodiments, an aggregate patient severity score 324 is generated from the severity indices 322 using statistical analysis 326, such as a rules-based aggregation method or technique. In an exemplary embodiment, the aggregate severity score 324 is generated automatically, such as by automatic implementation of the analysis 326 using suitable routines or computer-implemented code. In such embodiments, a reviewer or evaluator may simply be provided with an overall or aggregate severity score for the patient.

Figure 4:
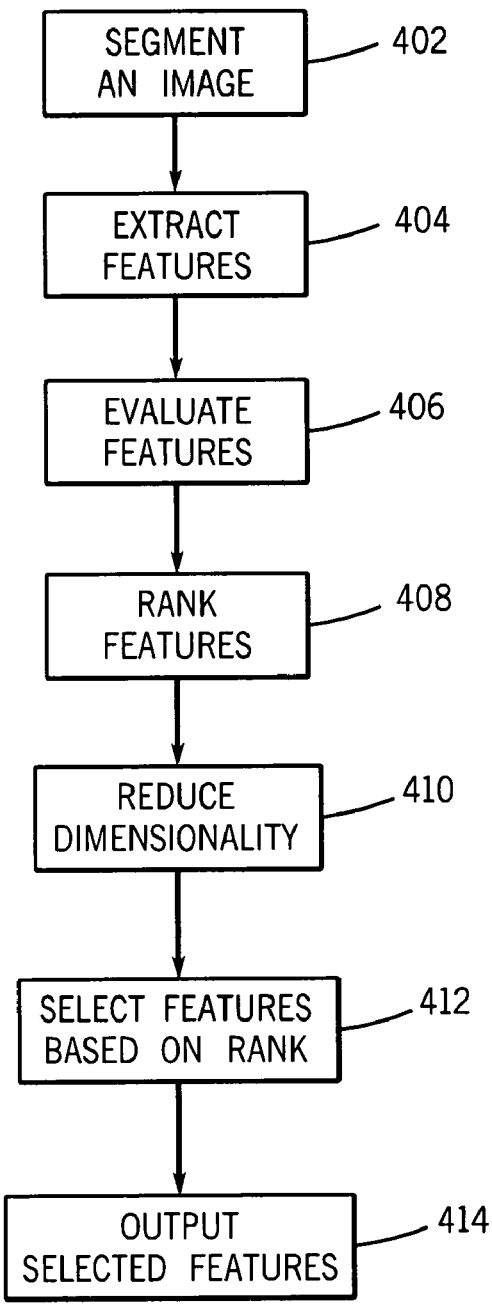
FIG. 4 is a flowchart of a method to select features in an image, in accordance with aspects of the present technique.

FIG. 4 is a flowchart depicting a method 400 for automatically selecting features in an image, such as deviation data 320, to facilitate the automated comparison described above with regard to FIG. 3. In accordance with an embodiment of this technique, an image, such as deviation data 320 or a reference image from disease severity deviation image sets 310, 312, 314, 316 is automatically processed to select features of interest. The image can have been acquired by various techniques and can be provided in various forms or formats. For example, the image data may have been acquired from a tomographic data source and may include diagnostic tomographic data. Example of suitable tomographic data include raw data in projection or Radon domains, single or multiple reconstructed two-dimensional images, i.e., slices, or a three-dimensional reconstructed volumetric image data set. Non-image information, such as patient history, may also be provided to facilitate the actions described below. As noted above, the image may also incorporate functional information acquired using a tracer and may, therefore, also be classifiable by the tracer or tracers employed.

In one embodiment, the image data is segmented (Block 402) to define a region of interest in the tomographic data from which features will be selected. The region of interest can be defined in several ways any may include the entire data set or only a part of the image data. For example, a specific region of the image data containing image data for a candidate mass may be segmented to facilitate feature extraction. The segmentation process itself may be accomplished using several techniques or combinations of techniques. Such techniques include, but are not limited to, iterative thresholding, k-means segmentation, edge detection, edge linking, curve fitting, curve smoothing, 2D/3D morphological filtering, region growing, fuzzy clustering, image/volume measurements, heuristics, knowledge-based rules, decision trees, and/or neural networks. The segmentation of the region of interest can be performed either manually and/or automatically. An example of a manual segmentation process may involve displaying the image data and allowing a user to delineate or otherwise designate the region using a mouse or any other suitable interface (e.g. touch screen, eye-tracking, voice commands). In an automated implementation, an automated segmentation algorithm can use prior knowledge such as the shape and size of a mass to automatically delineate the area of interest. Combinations of these types of techniques may also be employed to provide semi-automated segmentation techniques.

Features are automatically extracted (Block 404) from the image data or from a segmented region of interest if segmentation is employed. The feature extraction process involves performing computations on the provided image data. In one implementation, multiple feature measures are extracted from the image-based data using region of interest statistics such as shape, size, density, curvature, texture, intensity, gradient, edge strength, location, proximity, histogram, symmetry, eccentricity, orientation, boundaries, moments, fractal dimensions, entropy, and so forth. For projection space data, features such as location, shape, or size of feature projection in a view or location consistency from view-to-view may be extracted from the dataset. On acquisition-based and patient-based data, the data themselves may be the features extracted. Other factors may be incorporated into the feature extraction process, such as patient history (such as patient age, gender, smoking history, and so forth) and acquisition data (such as kVp and so forth).

Once extracted, the features are automatically evaluated (Block 406). In one embodiment, each feature is evaluated in terms of its ability to separate different classification groups, such as using distance criteria. In such an embodiment, various distance criteria can be used in evaluating the extracted features. Examples of such distance criteria include divergence, Bhattacharya distance, Mahalanobis distance, and so forth. In one such exemplary embodiment, the evaluated features are automatically ranked (Block 408) based on the evaluation criteria. For example, the evaluated features may be ranked based on a distance criteria by which they were evaluated.

The dimensionality of the resulting data set may be automatically reduced (Block 410) prior to further processing. For example, in one embodiment, features that are correlated with other desired features beyond a specified degree may be eliminated. In this manner, redundant or overly represented data may be removed from the data set.

The remaining features may be automatically selected (Block 412) until the performance or distinctiveness of the data set is no longer improved. For example, in one embodiment, the highest ranking feature is selected and additional features are selected and added in descending rank (i.e., the second highest ranking feature is added to the first, then the third highest ranking feature is added, and so forth.) In this implementation, additional features are no longer added when their addition does not improve the performance of the data set, such as for matching purposes and so forth. The set of features selected in this manner is automatically output (Block 414) for subsequent processing.

As will be appreciated by those of ordinary skill in the art, the automated feature selection process described with regard to FIG. 4 may be implemented using a pre-trained feature selection algorithm. As described above, such a feature selection algorithm may be employed to sort through the candidate features and select the useful features and remove those that provide no information or redundant information. Such a decision may be based on testing different classification results obtained using different combinations of candidate features. The feature selection algorithm may also be used to reduce the dimensionality from a practical standpoint, as noted above. Thus, a feature set may be derived that facilitates discriminating normal lesions from abnormal lesions. This selected feature set may be extracted on the regions of interest that are selected either automatically, manually, or semi-automatically, as noted above.

Figure 5:
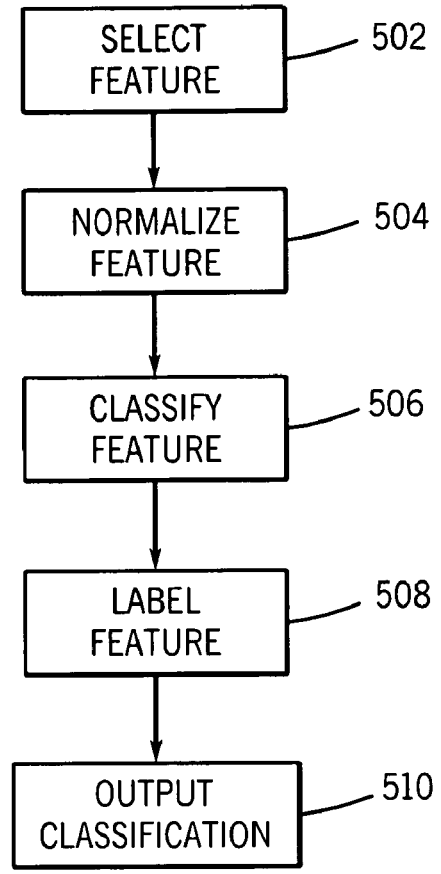
FIG. 5 is a flowchart of a method to classify features in an image, in accordance with aspects of the present technique.

Once the features are automatically selected, as described in FIG. 4, they are automatically classified, as described by Method 500 of FIG. 5. In accordance with one embodiment, the method of FIG. 5 is performed by a pre-trained classification algorithm, such as an algorithm that is trained to categorize the regions of interest into normal and abnormal lesions. As will be appreciated by those of ordinary skill in the art, various techniques may be employed in the feature classification scheme represented in FIG. 5. For example, Bayesian classifiers, neural networks, rule-based methods and/or fuzzy logic can be used for classification in accordance with the technique set forth by FIG. 5. Further it should be noted that the depicted classification process can be performed once by incorporating features from all of the data undergoing classification or can be performed in parallel. In a parallel implementation, the classification process or algorithm may be performed individually on each feature and the individual results subsequently combined, such as with an AND, an OR operation or a combination of both operations. In addition, the automatic classification process described herein can be performed in series or parallel to detect multiple diseases, such as by automatically classifying data associated with different anatomical features.

As noted above, the automated feature classification process described by FIG. 5 may be accomplished using a pre-trained classification algorithm. In such embodiments, the training of the algorithm may take the form of incorporating prior knowledge into the algorithm. For example, training the algorithm may involve performing computations for several candidate features on known samples of normal and abnormal lesions.

Turning now to FIG. 5, one or more features to be classified are selected (Block 502). Such feature selection may be accomplished using an implementation of the feature selection method 400 described with regard to FIG. 4, and as may be implemented by a pre-trained feature selection algorithm. Measures of the selected features are normalized (Block 504) with respect to feature measures derived from a database of known normal and abnormal cases. Feature measures that may be normalized in this manner include shape, size, density, curvature, texture, intensity, gradient, edge strength, location, proximity, histogram, symmetry, eccentricity, orientation, boundaries, moments, fractal dimensions, entropy, and so forth. In implementations where the feature classification process of FIG. 5 is implemented as a pre-trained classification algorithm, the algorithm may be trained using knowledge of the known normal and abnormal cases noted above, thereby providing a basis for normalizing feature measures with respect to such cases. The normalized features may be classified (Block 506). As will be appreciated by those of ordinary skill in the art, a variety of different classification techniques may be employed. For example, decision tree analysis, discriminant function analysis, Bayes' minimum-risk method, clustering techniques, and/or similarity measure approach may be employed to classify the normalized features. The classification process or technique may include grouping features that are identically or similarly classified and that should be evaluated together. Individual features or groups of similarly classified features may be labeled (Block 508) with their corresponding classification. The classified features or groups of features may be output (Block 510). As will be appreciated by those of ordinary skill in the art, the automated feature selection and classification techniques described with regard to FIGS. 4 and 5 may form the basis of the comparison process described with regard to FIG. 3 whereby deviation data 320 are compared to disease severity deviation images 310, 312, 314, 316. In this manner, the automated feature selection and classification processes described with regard to FIGS. 4 and 5 may directly and automatically lead to the assignment of a severity index 322 to each anatomical feature of interest for a patient. For example, the automated feature classification process may automatically match deviation data 320 with a corresponding image from a respective set of disease severity deviation images 310, 312, 314, 316 based on feature similarity. Based on this match, a severity index 322 associated with the matched reference image may be assigned to the respective deviation data 320.

Figures 6, 7:
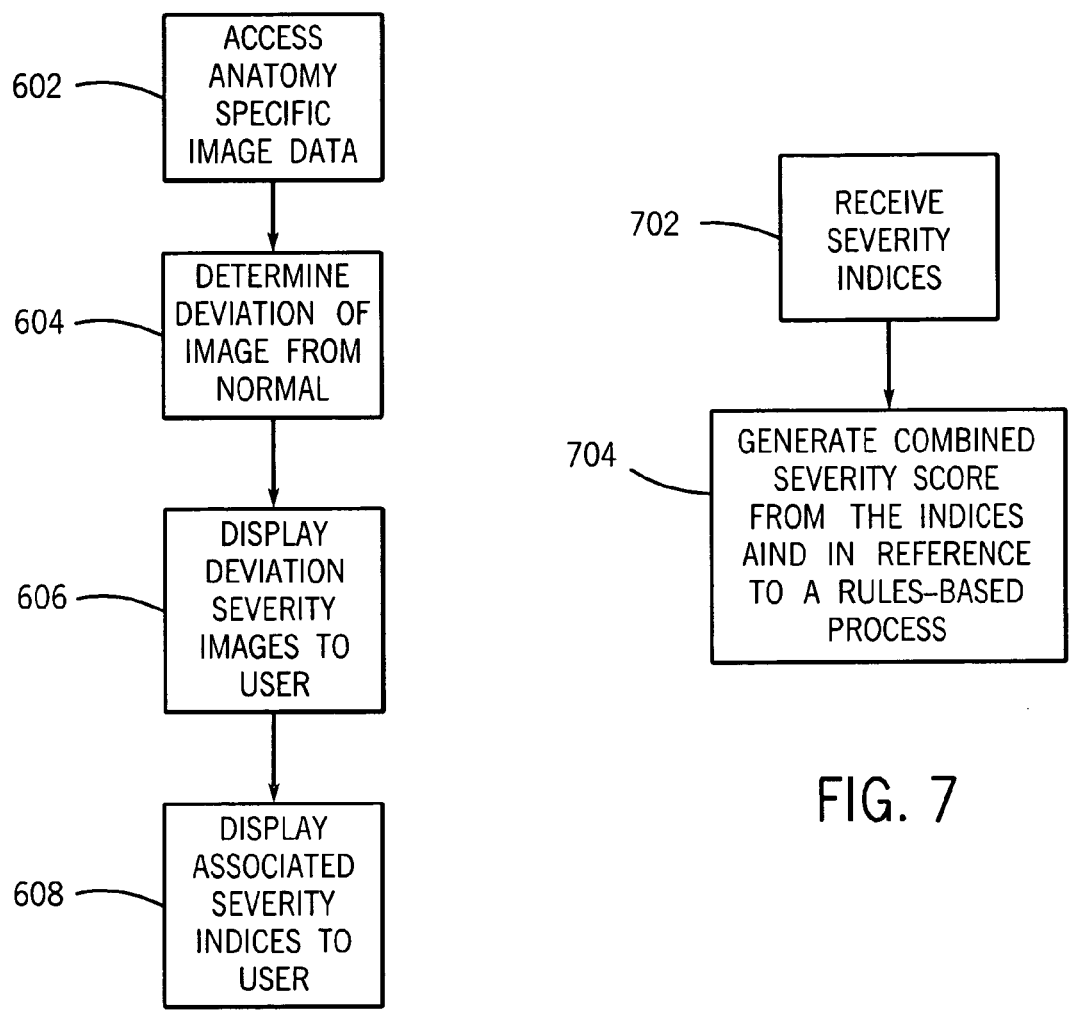
FIG. 6 is a flowchart of a method for generating and displaying deviation images and associated severities, in accordance with aspects of the present technique.
FIG. 7 is a flowchart of a method to generate a severity score, in accordance with aspects of the present technique.

While FIGS. 4 and 5 discuss methods for automatically selecting and classifying features that may lead to the automatic generation of a severity index 322 for each image of deviation data 320, FIG. 6 provides a more generalized description of the generation of a severity score. As will be appreciated by those of ordinary skill in the art, the technique of FIG. 6, though generalized, may also be implemented in an automated fashion, such as using an automated classification algorithm, to automatically generate severity indices 322 for respective deviation data 320. As depicted method 600 includes accessing image data (Block 602) that is specific to an anatomical feature, such as a brain or heart. In one embodiment, the image data of the anatomical feature includes functional information about the anatomical feature at the time of the imaging. For example, one or more tracers may be administered prior to image acquisition such that the resulting image of the anatomic features includes functional information attributable to the tracer or tracers or their byproducts. In some embodiments patients are imaged for specific anatomical and functional information using radiotracers or radiopharmaceuticals such as F-18-Deoxyglucose or Fluorodeoxyglucose (FDG), Ceretec®, Trodat®, etc. Each radiotracer provides separate, characteristic information pertaining to function and metabolism. In such implementations, patient images may be standardized corresponding to relevant tracer and age group to facilitate accessing the appropriate anatomy specific image data at block 602.

Method 600 also includes determining (Block 604) deviation data from the patient image data of the respective anatomical feature and from normative standardized anatomical image data. In one embodiment, factors such as the age and sex of the patient and the tracer or tracers used in generating the respective deviation data 320 are considered in determining the deviation data. For example, the age, and sex of the patient, and the tracers or tracers employed (if any) may be used to determine what normative standardized anatomical image data is used in the comparison. In some embodiments, the patient images and the normative standardized anatomical image data are compared pixel-by-pixel. In such embodiments, the patient images are standardized relative to one another in a manner that allows comparison to the respective normative standardized anatomical image data prior to determining the deviation data at block 604.

In some embodiments, the deviation data determined at block 604 may be displayed (Block 606) to a reviewer or evaluator, such as by displaying difference images or other visual representations that represent the deviations between the compared images. In such embodiments, difference images may be in the form of color or grey-scale representations of deviation from normalcy for each anatomical location and tracer. In other embodiments, the deviation data may be presented in other mediums, such on a printed medium, including paper or a printed photo. In automated implementations, however, the deviation data 320 may not be displayed to a viewer or may only be displayed after a pattern match has been automatically performed so that the viewer may evaluate the automated match.

For example, in some embodiments, the observed image deviation data determined at block 604 is used to automatically determine a degree of severity associated with the anatomical feature, i.e., a severity index 322, which may also be provided to a reviewer or evaluator by displaying (Block 608) or printing. The severity index 322 provides a quantification of the extent of disease, condition or abnormality of the anatomical feature, such as the brain or heart. As will be appreciated by those of ordinary skill in the art, the method 600 of FIG. 6 may be performed for multiple patient images and thus may generate multiple difference images and/or severity indices 322 for the same or different anatomical features. As noted above, the determination of deviation data and/or a severity index 322 for each respective image may be automated, such as by implementation of a suitable algorithm.

Referring now to FIG. 7, a method 700 is depicted for creating a medical diagnosis instructional aid, such as the aggregate patient severity score 324, according to one embodiment. Method 700 includes the act of receiving (Block 702) one or more severity indices 322, as described above. As noted above, each severity index 322 indicates the extent of disease in an anatomical structure in comparison to a non-diseased anatomical structure. As noted above, in an exemplary embodiment, each severity index 322 is automatically determined by comparing respective deviation data 320 with a corresponding set of disease severity deviation images 310, 312, 314, 316 that are ordered or otherwise associated with a known extent or amount of the disease or condition for the respective anatomical feature 302, 304, 306, 308. In one such embodiment, the severity index 322 is automatically determined by implementation of pre-trained feature selection and classification algorithms, as discussed above.

Method 700 also includes generating (Block 704) a combined severity score 324 from the severity indices 322 received in action 702. The combined severity score 324 is generated using a rules-based process in an exemplary embodiment. As noted above, the combined severity score 324 may be generated in an automated fashion using a rules-based technique or statistical analysis 326 implemented as an algorithm that accepts the severity scores 322 as inputs. For example, in one embodiment each anatomical and tracer severity index 322 is combined by an automated aggregation algorithm that implements a rules-based technique to generate a total severity score 324 for the disease state.

Figure 8:
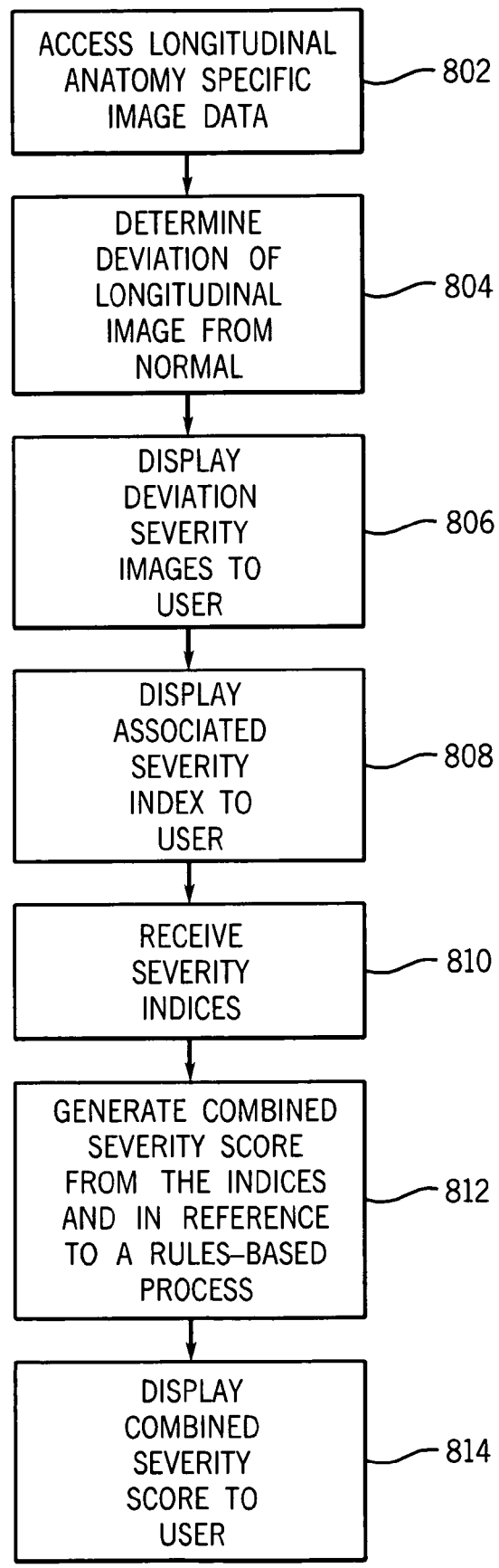
FIG. 8 is a flowchart of a method to identify a change in a status of a disease, in accordance with aspects of the present technique.

FIG. 8 is a flowchart of a method 800 to identify a change in a status of a disease over time according to an embodiment of the present technique. As will be appreciated by those of ordinary skill in the art, the change in status may be identified using techniques discussed above, such as the automated selection and automated classification of features. Accordingly, one or more pre-trained selection and/or classification algorithms which are automatically implemented may perform some of all of the functions described below.

Some embodiments of method 800 include accessing (Block 802) longitudinal, i.e., temporal, image data that is specific to at least two anatomical features over an interval of time. In one such embodiment, the longitudinal anatomical image data includes functional information based on at least one tracer in the anatomical feature at the time of imaging. The images may be acquired using any one of a number of conventional imaging techniques, such as the MRI, PET, CT, SPECT, ultrasound, and optical imaging modalities noted above. In one embodiment, patients are imaged for specific anatomical and functional information using tracers at two different times that may be separated from one another by days, weeks, months or years. Each tracer provides separate, characteristic information pertaining to function and metabolism. In an exemplary embodiment, patient images accessed at each time instance are standardized based on the relevant tracer or tracers and/or based on the age and/or sex of the patient.

Some embodiments of method 800 include determining (Block 804) deviation data from each of the longitudinal anatomical image data and from normative standardized anatomical image data, taking into account, the sex and age of the patient as well as any other patient specific factors of interest (patient history and so forth). Some embodiments of the act of determining the deviation data include comparing the anatomical longitudinal image data with normative standardized anatomical image data in reference to one or more tracers in the anatomical feature at the time of the imaging. As noted above, such a comparison may be performed using the automated selection and/or classification techniques described with regard to FIGS. 4 and 5. In some embodiments, images of each time instance in the longitudinal analysis are compared pixel by pixel to reference images of standardized normal patients.

In some embodiments method 800 also includes presenting (Block 806) to a reviewer or evaluator the severity data corresponding to the deviation of the patient images from the standardized normal images for each of the respective anatomical features. In some embodiments, the deviation data is in the form of deviation images that show the difference between the longitudinal anatomical image and the normative standardized anatomical image at each instance in time. Furthermore the difference images can be in the form of color or grey-scale representations of deviation from normalcy for each anatomical location and/or tracer and for every time instance in the longitudinal analysis. In an implementation employing automated selection and/or classification of features, such a display step may not be performed or may be performed subsequent to the automated classification process as part of a review or evaluation process.

In some embodiments method 800 includes presenting (Block 808) to the user a degree of severity, such as a severity index, associated with the respective deviations of each anatomical feature determined at block 804. For example, in an automated implementation, one or more feature selection and/or classification algorithms may automatically match deviation data associated with an image acquired at a given time with a similar reference image of known disease severity, i.e., a disease severity deviation image, as described above, thereby allowing a severity index to be automatically assigned to the deviation data.

In accordance with such an embodiment, method 800 also includes receiving (Block 810) a selected severity index for each longitudinal dataset based on the automated selection and classification performed at step 808. In those embodiments where selection and/or classification of features is performed automatically, the corresponding severity indices may be generated and received automatically without user intervention or involvement.

In certain embodiments method 800 also includes generating (Block 812) a combined severity score when multiple severity indices are present. In an exemplary embodiment, the act of generating the combined severity score may be performed automatically, such as by a suitably programmed algorithm executing a rule-based or statistical aggregation formula. In the context of a longitudinal analysis, such a severity score may represent the degree or severity of change over time. In some embodiments, the combined severity score is generated using a rules-based process. Some embodiments of generating a combined severity score include summing the severity indices using a rules-based process or performing some other mathematical or statistical operation in accordance with such rules-based processes. In some embodiments, each anatomical and tracer severity index is individually or comparatively (using the differences between instances of the longitudinal study) aggregated using a rules-based method to form a total changed severity score for the disease state at all instances of the longitudinal study. In one embodiment, both methods of change determination can be implemented such that one can be more indicative of anatomical location changes and the other provides an overall disease state severity score change. The severity scores or scores thus determined can be displayed (Block 814) to a reviewer or evaluator in an exemplary embodiment.

In some embodiments of method 800, accessing 802 the longitudinal image data, determining 804 the deviation, presenting 806 and 808 and receiving 810 the severity indices are performed a number of times before generating 812 and displaying 814 the combined severity score. In some embodiments, a number of severity indices are displayed for the specific anatomy over a time period, which shows progress, or lack of progress of treatment of the disease over the time period.

Figure 9:
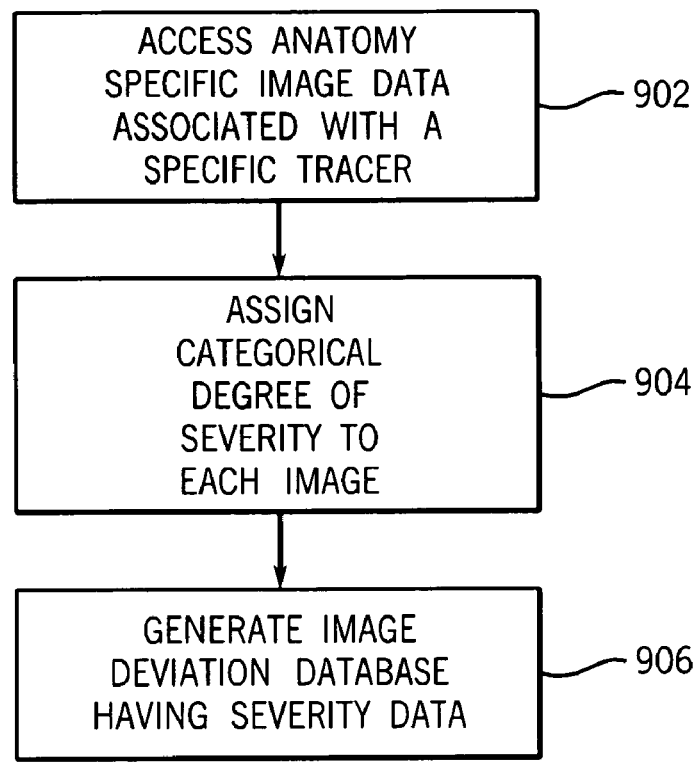
FIG. 9 is a flowchart of a method to create an exemplary or normal knowledge base of diagnostic medical images, in accordance with aspects of the present technique.

FIG. 9 is a flowchart of a method 900 to create an exemplary or normal knowledge base of diagnostic medical images according to an embodiment of the present technique. In some embodiments, deviation data is derived prior to the depicted acts of method 900. In such embodiments, the deviation data may be derived by comparing images from a normal subject database and a suspected disease image database, including data pertaining to severity of a disease, such as described in method 1000 in FIG. 10 below. As will be appreciated by those of ordinary skill in the art, such deviation data generally represents deviation or differences from an image that is considered to be representative of normal anatomical conditions or non-diseased anatomy. In varying embodiments an image from which image deviation data is derived may be created or generated with or without the use of a tracer in the patient.

In an exemplary embodiment, method 900 includes accessing (Block 902) one or more images of one or more specific anatomical features that are associated with a specific tracer. In such an embodiment, method 900 may include assigning (Block 904) a categorical degree of severity to each image of deviation data exhibiting functional image characteristics corresponding to the degree of severity. The categorical degree of severity describes the extent of the severity of disease or medical condition within a certain range. In some embodiments, the categorical degree of severity describes a measure of a deviation of an image from an exemplary or normal image. Examples of degrees of a disease or condition are described with regard to FIG. 3, where disease severity deviation images 310, 312, 314, 316 are ordered based upon their respective categorical degree of severity of disease or condition.

In certain embodiments, method 900 includes generating (Block 906) a database or knowledgebase of the image deviation data and the categorical degree of severity corresponding to each image of the image deviation data. In one example, the normal image database 102 in FIG. 1 is generated or updated with the image deviation data and with the associated categorical degree of severity for each image of the image deviation data.

Some embodiments of method 900 also include refining or updating exemplary severity deviation images. For example, the exemplary severity deviation database may be refined by aggregating new or additional image deviation data and corresponding severity categories with existing severity image/images. In addition, the exemplary severity deviation images may be updated by introducing additional severity categories or removing existing categories. Similarly, the exemplary severity deviation images may be updated by introducing image data corresponding to new anatomical features and/or tracers or by removing existing data corresponding to particular anatomical features and/or tracers.

Figure 10:
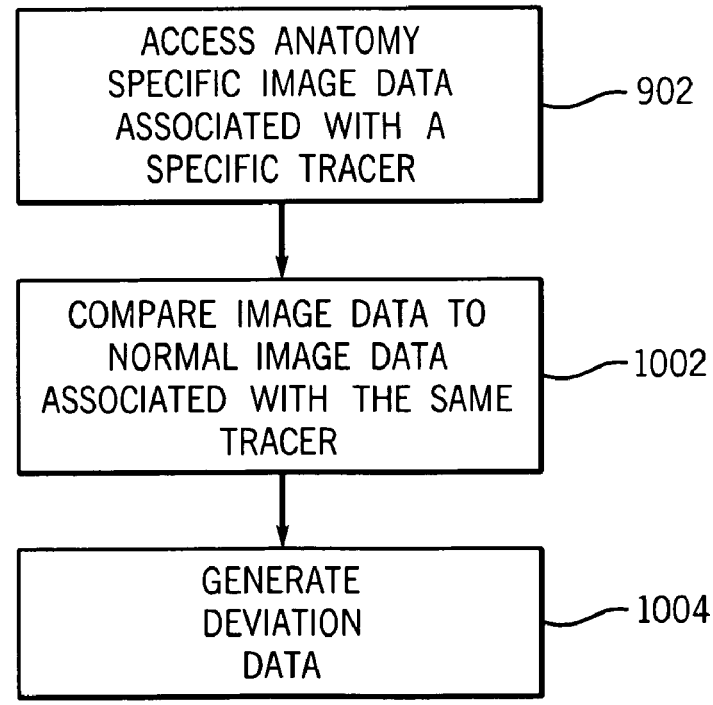
FIG. 10 is a flowchart of a method to generate deviation data, in accordance with aspects of the present technique.

FIG. 10 is a flowchart of a method 1000 to generate deviation data according to an embodiment of the present technique. Method 1000 can be performed before method 900, discussed above, to generate deviation data that may be utilized in method 900. Method 1000 includes accessing (Block 902) one or more images of one or more specific anatomical features, such as a brain or heart, that are associated with a specific tracer.

In the depicted embodiment, method 1000 also includes comparing (Block 1002) the anatomical feature image data with normative standardized anatomical image data, to yield deviation data for the images that represent suspect areas of disease in the patient image data with images in a database. Some embodiments of the act of comparing 1002 utilize patient and/or database images generated using a tracer. In other embodiments, however, the act of comparing 1002 does not utilize patient and/or database images generated using a tracer. Some embodiments of method 1000 also include generating (Block 1004) deviation image data, such as a difference image, from the comparison.

Figure 11:
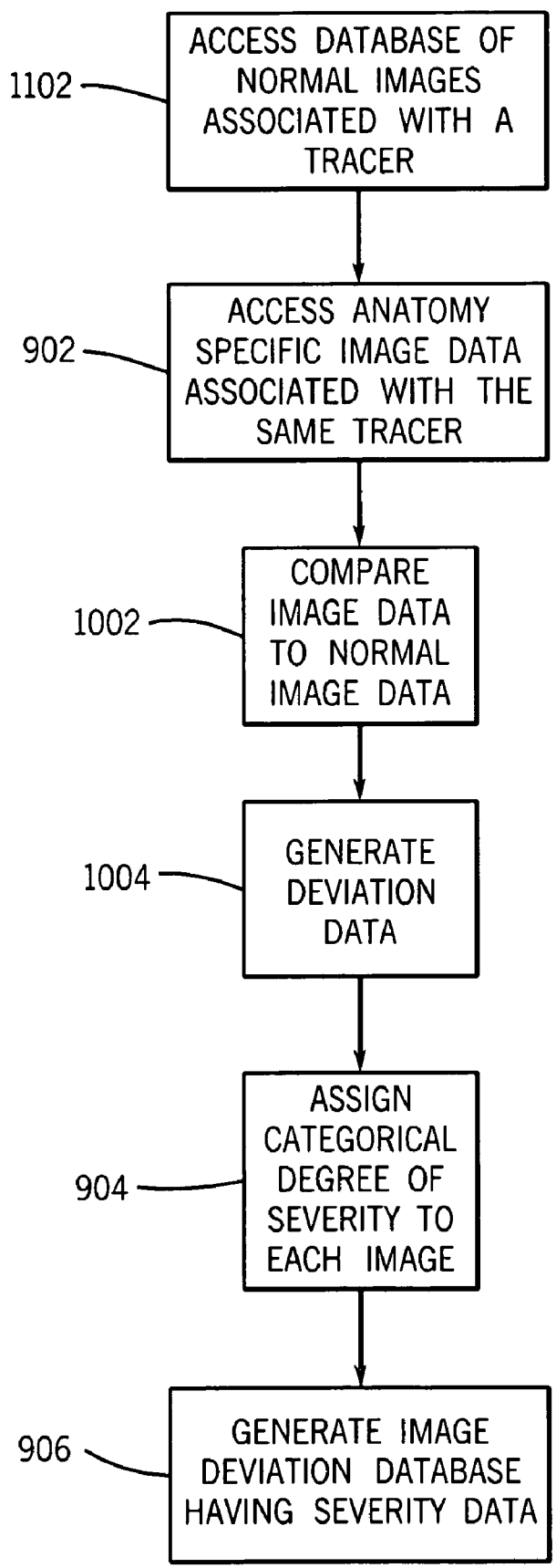
FIG. 11 is a flowchart of a method to generate reference diagnostic medical images, in accordance with aspects of the present technique.

FIG. 11 is a flowchart of a method 1100 to generate reference diagnostic medical images according to an embodiment of the present technique. Method 1100 includes accessing (Block 1102) a database of images of a normal pre-clinical anatomical feature acquired using a tracer. In some embodiments, the act of accessing 1102 includes creating a normative database of functional image data acquired from normal subjects using one or more tracers.

In an exemplary implementation, method 1100 includes accessing (Block 902) images that represent suspect areas of disease in the anatomical feature, comparing (Block 1002) the images that represent suspect areas of disease in the anatomical feature with images in the database, thus yielding deviation image data representing differences between the images that represent suspect areas of disease in the anatomical feature with images in the database. In some embodiments, accessing the images includes accessing a database of suspect images that have functional information corresponding to different severities of a disease and that can be compared with the other images acquired using the same tracer.

In one embodiment, one or more images representing the deviation may be generated (Block 1004) for each anatomical feature. In such an embodiment, a categorical degree of severity is assigned (Block 904) to each of the deviation images and a database of the deviation images and the associated categorical degree of severity of each deviation image is generated (Block 906). In some embodiments of method 1100, the exemplary severity deviation database may be refined by adding new or additional image deviation data and corresponding severity categories into the database. In addition, the exemplary severity deviation database may be updated by introducing additional severity categories, by adding new image data with the associated new severity categories or by revising the severity categories assigned to existing images in the database. Similarly, the exemplary severity deviation database may be updated by introducing image data corresponding to new anatomical features and/or tracers or by removing existing data corresponding to particular anatomical features and/or tracers.

In some embodiments, methods 200-1100 are implemented as routines executable by a computer. Such routines typically represent a sequence of instructions which, when executed by a processor, such as processor 1204 in FIG. 12, cause the processor to perform the respective actions or steps of the present techniques. Such routines may be stored on one or more computer-readable media that may be accessed by a processor, such as processor 1204 in FIG. 12, to perform the respective techniques. Such a computer-readable medium may be a magnetic medium, an electronic medium, or an optical medium.

More specifically, in an embodiment where one or more computer readable media are provided that include routines for performing some or all of the technique discussed herein, the routines can be prepared using an object-oriented language such as Java, Smalltalk or C++ or the routines can be prepared using a procedural language such as COBOL or C. The software components communicate in any of a number of means that are well-known to those skilled in the art, such as application program interfaces (API) or interprocess communication techniques such as remote procedure call (RPC), common object request broker architecture (CORBA), Component Object Model (COM), Distributed Component Object Model (DCOM), Distributed System Object Model (DSOM) and Remote Method Invocation (RMI). The software components can be execute on a single computer, such as the computer 1402 in FIG. 12, or on multiple computers.

Hardware and Operating Environment

FIG. 12 is a block diagram of the hardware and operating environment 1400 in which different embodiments of the present technique can be practiced. The description of FIG. 12 provides an overview of computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

Computer 1202 includes a processor 1204, such as a processor commercially available from Intel, Motorola, Cyrix or others. Computer 1202 also includes random-access memory (RAM) 1206, read-only memory (ROM) 1208, and one or more mass storage devices 1210, and a system bus 1212, that operatively couples various system components to the processing unit 1204. The memory 1206, 1208, and mass storage devices, 1210, are types of computer-accessible media. Mass storage devices 1210 are typically types of nonvolatile computer-accessible media and can include one or more hard disk drives, floppy disk drives, optical disk drives, or tape cartridge drives. The processor 1204 executes computer programs stored on the computer-accessible media.

Computer 1202 can be communicatively connected to the Internet 1214 via a communication device 1216. In one embodiment, a communication device 1416 is a modem that responds to communication drivers to connect to the Internet via what is known in the art as a "dial-up connection." In another embodiment, a communication device 1216 is an Ethernet® or similar hardware network card connected to a local-area network (LAN) that itself is connected to the Internet via what is known in the art as a "direct connection" (e.g., T1 line, etc.).

A user enters commands and information into the computer 1202 through input devices such as a keyboard 1218 or a pointing device 1220. The keyboard 1218 permits entry of textual information into computer 1202, as known within the art, and embodiments are not limited to any particular type of keyboard. Pointing device 1220 permits the control of the screen pointer provided by a graphical user interface (GUI) of operating systems such as versions of Microsoft Windows®. Embodiments are not limited to any particular pointing device 1220. Such pointing devices include mice, touch pads, trackballs, remote controls and point sticks. Other input devices (not shown) can include a microphone, joystick, game pad, satellite dish, scanner, or the like.

In some embodiments, computer 1202 is operatively coupled to a display device 1222 connected to the system bus 1212. Display device 1222 permits the display of information, including computer, video and other information, for viewing by a user of the computer. Embodiments are not limited to any particular display device 1222. Such display devices include cathode ray tube (CRT) displays (monitors), as well as flat panel displays such as liquid crystal displays (LCD's). In addition to a monitor, computers typically include other peripheral input/output devices such as printers (not shown). Speakers 1224 and 1226 provide audio output of signals. Speakers 1224 and 1226 are also connected to the system bus 1212.

Computer 1202 also includes an operating system (not shown) that is stored on the computer-accessible media RAM 1206, ROM 1208, and mass storage device 1210, and is and executed by the processor 1204. Examples of operating systems include Microsoft Windows®, Apple MacOS®, Linux®, UNIX®. Examples are not limited to any particular operating system, however, and the construction and use of such operating systems are well known within the art.

Embodiments of computer 1202 are not limited to any type of computer 1202. In varying embodiments, computer 1202 comprises a PC-compatible computer, a MacOS®-compatible computer, a Linux®-compatible computer, or a UNIX®-compatible computer. The construction and operation of such computers are well known within the art.

Computer 1202 can be operated using at least one operating system to provide a graphical user interface (GUI) including a user-controllable pointer. Computer 1202 can have at least one web browser application program executing within at least one operating system, to permit users of computer 1202 to access an intranet, extranet or Internet world-wide-web pages as addressed by Universal Resource Locator (URL) addresses. Examples of browser application programs include Netscape Navigator®and Microsoft Internet Explorers®.

The computer 1202 can operate in a networked environment using logical connections to one or more remote computers, such as remote computer 1228. These logical connections are achieved by a communication device coupled to, or a part of, the computer 1202. Embodiments are not limited to a particular type of communications device. The remote computer 1228 can be another computer, a server, a router, a network PC, a client, a peer device or other common network node. The logical connections depicted in FIG. 12 include a local-area network (LAN) 1230 and a wide-area network (WAN) 1232. Such networking environments are commonplace in offices, enterprise-wide computer networks, intranets, extranets and the Internet.

When used in a LAN-networking environment, the computer 1202 and remote computer 1228 are connected to the local network 1230 through network interfaces or adapters 1234, which is one type of communications device 1216. Remote computer 1228 also includes a network device 1236. When used in a conventional WAN-networking environment, the computer 1202 and remote computer 1228 communicate with a WAN 1232 through modems (not shown). The modem, which can be internal or external, is connected to the system bus 1212. In a networked environment, program modules depicted relative to the computer 1202, or portions thereof, can be stored in the remote computer 1228.

Computer 1202 also includes power supply 1238. The power supply can be a battery or an AC power connection.

Apparatus Embodiments

Figure 13:
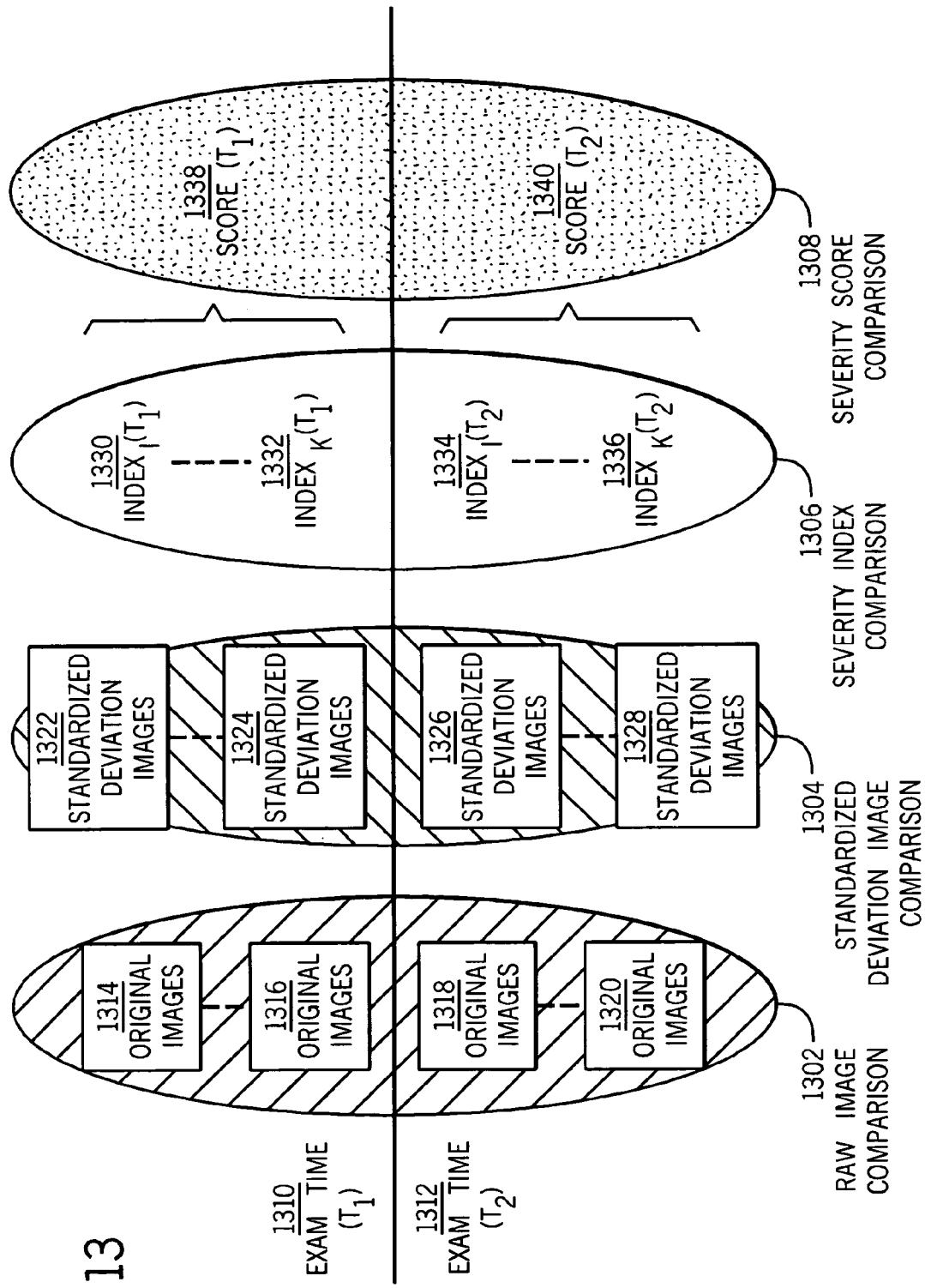
FIG. 13 is a block diagram of an apparatus to generate reference diagnostic medical images, in accordance with aspects of the present technique.

FIG. 13 is a block diagram of an apparatus 1300 to generate reference diagnostic medical images according to an embodiment of the present technique. In apparatus 1300, four different comparisons can be performed on the image data; a comparison (Block 1302) of raw images, a comparison (Block 1304) of standard deviation images, a comparison (Block 1306) of severity images, and a comparison (Block 1308) of severity scores. The comparison can happen at any of the stages 1302, 1302, 1306 or 1308. In the depicted embodiment, each of the comparisons 1302-1308 are performed across longitudinal (temporal) domains, such as Examination Time $T_1$ 1310 and Examination Time $T_2$ 1312.

At Examination Time $T_1$ 1310 and Examination Time $T_2$ 1312, a plurality of raw original images 1314 and 1316, 1318 and 1320 respectively are generated by a digital imaging device. After Examination Time $T_1$ 1310 and Examination Time $T_2$ 1312, any one of the following three data are generated from the raw original images and from one or more standardized images (not shown): a plurality of standardized deviation images 1322 and 1324, and 1326 and 1328; severity indices 1330-1336 or severity scores 1338 and 1340. The deviation images 1322-1328 graphically represent the deviation between the raw original images 1314-1320 and the standardized images. The severity indices 1330-1336 numerically represent clinically perceived deviation between the raw original images 1314-1320 and the standardized images. The severity scores 1338 and 1340 are generated from the severity indices 1330-1336. The severity scores 1338 and 1340 numerically represent a composite clinical indication of the condition of the raw images 1314-1320.

CONCLUSION

A computer-based medical diagnosis system is described. Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations. For example, although described in procedural terms, one of ordinary skill in the art will appreciate that implementations can be made in a procedural design environment or any other design environment that provides the required relationships without departing from the scope of the concepts described herein.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future communication devices, different file systems, and new data types. Furthermore, the terminology used in this application is meant to include all object-oriented, database and communication environments and alternate technologies which provide the same functionality as described herein.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method to create a normative categorical score of medical diagnostic images, the method comprising:
   accessing an acquired image of an anatomical region of a patient, the acquired image depicting functional information regarding at least one tracer in the anatomical region at the time of the imaging;
   generating, on a computer, a deviation image visually depicting the deviation of the acquired image from normative standardized anatomical image data based on one or more subject specific factors, wherein the deviation image represents the degree and manner in which the acquired image deviates from the corresponding normative standardized anatomical image data for the anatomical feature; and
   comparing, on a computer, the generated deviation image with an existing database of disease severity images, each database image visually depicting a respective deviation from normality for the anatomical region and each corresponding to a respective severity index value.

2. The method of claim 1, comprising generating a combined severity score from a plurality of severity index values in reference to a rules-based process.

3. The method of claim 2, wherein generating the combined severity score comprises summing the plurality of severity indices in reference to a rules-based process.

4. The method of claim 1, wherein the one or more subject-specific factors comprise at least one of an age of the subject or a sex of the subject.

5. The method of claim 1, comprising acquiring the acquired image positron emission tomography, computed tomography, single photon emission computed tomography, ultrasound or optical imaging.

6. The method of claim 1, wherein generating the deviation image comprises comparing the acquired image of the anatomical region with normative standardized image data for the respective anatomical region and taking into account at least one tracer in the anatomical region at the time of the imaging.

7. The method of claim 1, wherein comparing comprises selecting one or more features within the deviation image for comparison to a set of disease severity deviation images categorized into a degree of severity for the anatomical region.

8. The method of claim 1, wherein comparing comprises classifying one or more features within the deviation image based on a comparison to a set of disease severity deviation images categorized into a degree of severity for the anatomical region.

9. One or more non-transitory computer readable media, comprising code executable to perform the acts of:
   accessing an acquired image of an anatomical region of a patient, the acquired image depicting functional information regarding at least one tracer in the anatomical region at the time of the imaging
   generating a deviation image visually depicting the deviation of the acquired image from normative standardized anatomical image data based on one or more subject specific factors, wherein the deviation image represents the degree and manner in which the acquired image deviates from the corresponding normative standardized anatomical image data for the anatomical feature; and
   comparing the generated deviation image with an existing database of disease severity images, each database image visually depicting a respective deviation from normality for the anatomical region and each corresponding to a respective severity index value.

10. The one or more non-transitory computer readable media of claim 9, further comprising code executable to perform the acts of:
    generating a combined severity score from a plurality of severity index values in reference to a rules-based process.

11. The one or more non-transitory computer readable media of claim 10, wherein the code executable to generate the combined severity score sums the plurality of severity indices in reference to a rules-based process.

12. The one or more non-transitory computer readable media of claim 9, wherein the one or more subject-specific factors comprise at least one of an age of the subject or a sex of the subject.

13. The one or more non-transitory computer readable media of claim 9, further comprising code executable to perform the acts of:
    acquiring the acquired image of the anatomical region using one of magnetic resonance imaging, positron emission tomography, computed tomography, single photon emission computed tomography, ultrasound or optical imaging.

14. The one or more non-transitory computer readable media of claim 9, wherein the code executable to generate the deviation image compares the acquired image of the anatomical region with normative standardized image data for the respective anatomical region and takes into account at least one tracer in the anatomical region at the time of the imaging.

15. The one or more non-transitory computer readable media of claim 9, wherein the at least one specific anatomical region comprises at least a portion of a brain.

16. The one or more non-transitory computer readable media of claim 9, wherein the at least one tracer comprises a radioactive tracer.

17. The one or more non-transitory computer readable media of claim 9, wherein the code executable to compare selects one or more features within the deviation image for comparison to a set of disease severity deviation images categorized into a degree of severity for the anatomical region.

18. The one or more non-transitory computer readable media of claim 9, wherein the code executable to compare classifies one or more features within the deviation image based on a comparison to a set of disease severity deviation images categorized into a degree of severity for the anatomical region.

19. A method for automatically generating a severity score, comprising:
    generating, on a computer, a severity index for each of a plurality of patient images by matching a respective deviation image generated for each patient image with a respective reference image of a set of reference deviation images, wherein each generated deviation image represents a degree and manner in which the respective patient image deviates from a corresponding anatomical image depicting a corresponding anatomical region in a non-diseased state; and
    deriving, on a computer, a severity score based on the plurality of severity indexes.

20. The method of claim 1, wherein the deviation image comprises a Z-score image visually depicting the statistical degree of deviation of the acquired image of the anatomical region from a normal image of the anatomical region and wherein the existing database of disease severity images comprises a plurality of Z-score images each visually depicting the statistical degree of deviation of each respective database image from normality.

21. The method of claim 1, wherein the deviation image comprises a difference image visually depicting the mathematical difference between the acquired image of the anatomical region from a normal image of the anatomical region and wherein the existing database of disease severity images comprises a plurality of difference images each visually depicting the mathematical difference between each respective database image and a non-diseased image of the anatomical region.

* * * * *